United States Patent [19]

Sugahara et al.

[11] 4,349,426
[45] Sep. 14, 1982

[54] ANION SENSING ELECTRODE

[75] Inventors: Kenshi Sugahara, Katsuta; Junji Mori, Hitachi, both of Japan

[73] Assignee: Hitachi, Ltd., Tokyo, Japan

[21] Appl. No.: 200,458

[22] Filed: Oct. 24, 1980

[30] Foreign Application Priority Data

Oct. 26, 1979 [JP] Japan .................. 54-139026

[51] Int. Cl.$^3$ ............................ G01N 27/46
[52] U.S. Cl. .................. 204/195 M; 204/1 T
[58] Field of Search ............. 204/1 T, 195 P, 195 M, 204/195 L, 1 B; 23/230 B

[56] References Cited

U.S. PATENT DOCUMENTS

| | | | |
|---|---|---|---|
| 3,429,785 | 2/1969 | Ross | 204/195 L |
| 3,723,281 | 3/1973 | Wise | 204/195 L |
| 3,801,486 | 4/1974 | Wise | 204/195 L |
| 4,134,798 | 1/1979 | Pinsky | 204/195 M |

FOREIGN PATENT DOCUMENTS 54-89688 7/1979 Japan .

OTHER PUBLICATIONS

Moody et al., "Chemistry & Industry", Aug. 17, 1974, pp. 644–647.

*Primary Examiner*—T. Tung
*Attorney, Agent, or Firm*—Craig and Antonelli

[57] ABSTRACT

A sensing membrane is fixed to one end of a tube comprising polyvinyl chloride. An aqueous sodium chloride solution is contained in the tube, and is in contact with an internal electrode wire. The sensing membrane comprises a support substance of polyvinyl chloride, a sensing substance of quaternary ammonium salt having an alkyl chain having 8 to 16 carbon atoms, and a plasticizer of normal decyl alcohol. Anions in a body fluid sample can be measured with a small measurement error by an electrode provided with the sensing membrane of that composition.

11 Claims, 5 Drawing Figures

ANION SENSING ELECTRODE

BACKGROUND OF THE INVENTION

This invention relates to an anion sensing electrode, and more particularly to an anion sensing electrode having a support membrane of polymeric material.

Ion sensing electrodes are widely used for measuring ions in a body fluid sample. Some of the ion sensing electrodes has a polymeric membrane containing an anion sensing substance therein. For example, U.S. Pat. No. 3,801,486 discloses a chloride sensing electrode having a cellophane membrane. Japanese Laid-open Patent Application Specification No. 89688/79 discloses an anion sensing electrode having a sensing membrane containing polyvinyl chloride as a support substance, a quaternary ammonium salt as a sensing substance, and phenylalkylalcohol as a plasticizer.

SUMMARY OF THE INVENTION

An object of the present invention is to provide an anion sensing electrode having a small measurement error when a body fluid sample is measured.

Another object of the present invention is to provide an anion sensing electrode capable of reducing adsorption of inhibiting substances in a body fluid sample.

The present invention has been established in view of the fact that the conventional anion sensing electrode having a sensing membrane is liable to adsorb inhibiting substances in a body fluid sample when used to measure the body fluid sample.

The present invention is characterized by a composition of a sensing membrane. The present sensing membrane contains a polymeric substance as a support substance, a quaternary ammonium salt as a sensing material, and an aliphatic alcohol having 8 to 16 carbon atoms as a plasticizer. The sensing substance and the plasticizer are distributed in the membrane at appropriately selected concentrations and supported by the support substance.

DETAILED DESCRIPTION OF THE PREFERRED EMBODIMENTS

In the present invention, an aliphatic quaternary ammonium salt is used as an ion exchanger serving as an ion sensing substance, and ammonium salts having alkyl chains of 8 to 16 carbon atoms, such as methyl-n-tridodecylammonium chloride, methyl-n-tetradecylammonium chloride, methyl-n-trioctylammonium chloride, etc. are preferably used as the ammonium salt.

According to a preferable embodiment of the present invention, a normal chain aliphatic alcohol is used as a plasticizer, and n-tetradecyl alcohol having a hydroxyl group —OH at its terminal end 14 carbon atoms is most preferably used. The smaller the number of carbon atoms of the aliphatic alcohol, the more increased is a solubility in water. Below less than 7 carbon atoms, dissolution of the plasticizer from the membrane into a sample solution takes place rapidly, and this is not substantially practical. Aliphatic alcohol having 15 or more carbons has a smaller solubility in water and an increasing crystallinity. However, aliphatic alcohol having 17 or more carbon atoms is not suitable as the plasticizer. n-Tetradecyl alcohol used in the embodiment of the present invention is crystalline at the normal temperature, but has a low solubility in water, and acts as a liquid plasticizer under an internal pressure exerted by molecular movement among polyvinyl chloride segments in a polyvinyl chloride support membrane, and thus it is a particularly preferable plasticizer.

Protein ions in a body fluid behave as ampho-ions having both anions and cations such as ammonium group, carboxyl group, etc. as intramolecular ions. In order to reduce the influence of protein ions in a body fluid, it is thus keenly desired to use a plasticizer as unsusceptible as possible to chemical bonding or reaction with these anions and cations. Thus, a plasticizer having a hydroxyl group —OH in the molecular structure, such as n-tetradecyl alcohol, is very effective for reducing the adsorption of protein onto the surface of a sensing membrane through the anions and cations of protein. At the same time, it can make dissolution of a sensing substance as small as possible owing to the low solubility in water.

On the other hand, a polymeric substance as a support membrane material for supporting a sensing substance or a plasticizer is practically polyvinyl chloride, polycarbonate, silicone rubber, etc. Particularly in the case of body fluid sample as serum, polyvinyl chloride is suitable. Polyvinyl chloride is more advantageous in processability than other support membrane substances.

Figure 1:
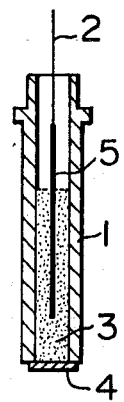
FIG. 1 is a cross-sectional view of a schematic structure of one embodiment of the present invention.

FIG. 1 shows a schematic, cross-sectional structural view of an anion sensing electrode according to one embodiment of the present invention. An electrode body 1 of polyvinyl chloride cylinder contains an inner filling solution 3 and an inner electrode element 2 is immersed in the inner filling solution 3. An ion sensing membrane 4 is provided at the lower end of body 1. The sensing membrane 4 is made from a polyvinyl chloride support film, in which a quaternary ammonium salt and an aliphatic alcohol are distributed at appropriate concentrations in percent by weight.

The anion sensing electrode shown in FIG. 1 is prepared in the following manner.

Methyltridodecylammonium chloride as a sensing substance is weighed out so that it can be contained in a support membrane at a concentration of 10–20% by weight; n-tetradecyl alcohol as a plasticizer is weighed out so that it can be contained in the support membrane at a concentration of 20–40% by weight; and polyvinyl chloride as a membrane support material is weighed out so that it can be contained at a concentration of 40–60% by weight, making total 100% by weight, and they are mixed and dissolved in tetrahydrofuran. The resulting solution is poured into a desired mold, and then tetrahydrofuran is removed therefrom by drying, thereby forming a sheet of chloride ion sensing membrane. A disk is cut out from the sheet, and fixed to the lower end of cylindrical body 1 made from polyvinyl chloride by adhesion as shown in FIG. 1. Then, an aqueous $10^{-2}$ M sodium chloride (NaCl) solution is placed into the body 1 as the inner filing solution 3. Then, a silver wire provided with a coating 5 of silver-silver chloride is inserted into the inner filling solution as an internal electrode element 2, and an electrode output is led to an amplifier through the internal electrode element to measure an electromotive force.

Then, a composition ratio of the sensing substance, the plasticizer and the support membrane substance in the sensing membrane and test results on relationships between the composition ratio and the electrode performance of the sensing membrane will be described in detail below.

Figure 2:
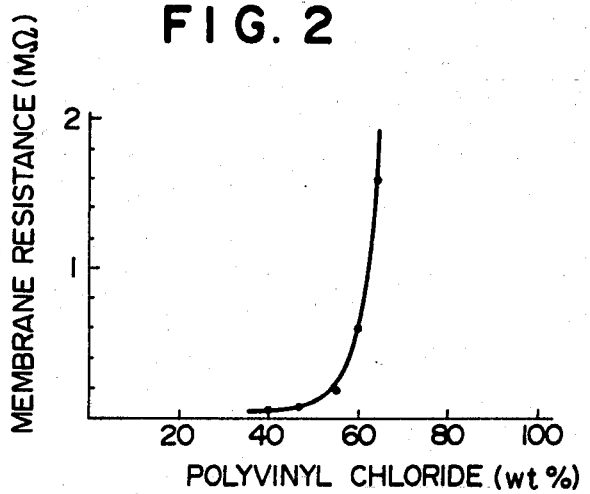
FIG. 2 is a diagram showing relationships between percent by weight of polyvinyl chloride as a support substance and membrane resistance.

In FIG. 2, relationships between percent by weight of polyvinyl chloride as a support membrane substance and resistance of electrode membrane are shown. In the test, a ratio of methyltridodeclyammonium chloride as a sensing substance to n tetradecyl alcohol as a plasticizer is kept at 1:2. As is obvious from FIG. 2, the membrane resistance is drastically increased when percent by weight of polyvinyl chloride exceeds about 60%. The increase in the membrane resistance means a low concentration of the sensing material in the support membrane. Furthermore, when a large number of electrodes are used, an increase in the membrane resistance gives rise to fluctuation among the electrodes. At less than 40% by weight of polyvinyl chloride, the function as a membrane is lost. Thus, preferable percentage by weight of the support membrane substance in the sensing membrane is 40-60%.

Figure 3:
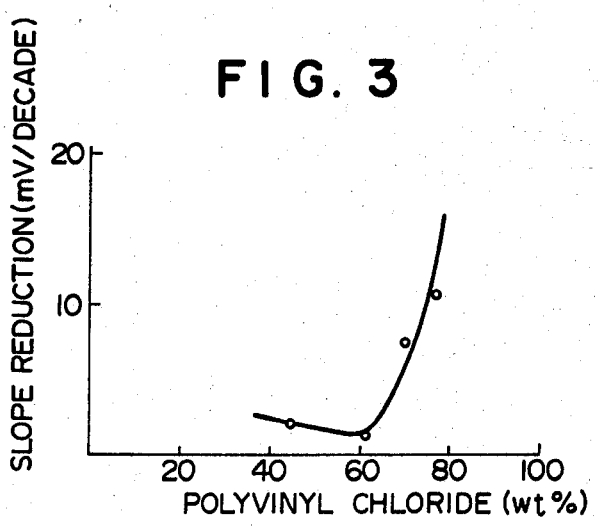
FIG. 3 is a diagram showing relationships between percent by weight of polyvinyl chloride as a support substance and slope reduction.

In FIG. 3, relationships between percent by weight of polyvinyl chloride and slope reduction (change), most important factor among the electrode performances when 300 serum samples were measured are shown. The term "slope" used herein is generally defined as follows: an ion sensing electrode is a sensor utilizing an electrochemical energy, and thus an electromotive force generated by the sensor is given by the following equation:

$$E = E_o \pm S \log a$$

wherein

E: electromotive force $E_o$: value determined by a given measuring system a: ion activity of specific ion to be measured in sample S: difference in electromotive force when the ion activity is changed by one order of magnitude, that is, slope (gradient).

As is obvious from FIG. 3, preferable percent by weight of polyvinyl chloride is 40-60%, which is in good agreement with the results of FIG. 2.

Figure 4:
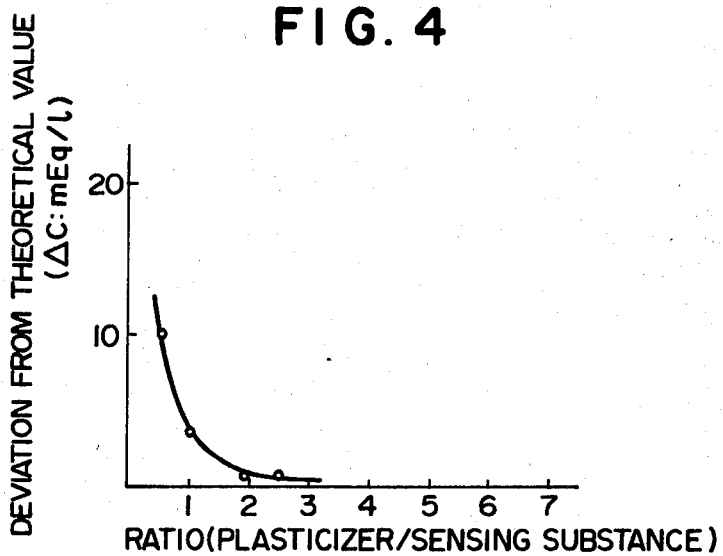
FIG. 4 is a diagram showing relationships between a ratio of a plasticizer to a sensing substance and a deviation of found chloride ion concentration from theoretical value.

In FIG. 4, deviation ($\beta c$:mEq/l) of found chloride ion concentration in serum from theoretical value when the ratio of a plasticizer to a sensing substance is changed while keeping percent by weight of polyvinyl chloride constant at 55% is shown. As is evident from FIG. 4, the deviation from the theoretical value can be substantially disregarded, if the ratio of a plasticizer to a sensing substance is at least 1.5.

The foregoing test results show that an appropriate composition can be selected in view of an electrode life, deviation from theoretical value, stability and reliability of electrode, etc. It has been found that the composition of a sensing membrane with the best results is in a ratio by weight of a plasticizer to a sensing substance of 1:2, and percent by weight of polyvinyl chloride of 55%. That is, when the concentration of polyvinyl chloride is 55% by weight, a composition rate of a sensing substance: a plasticizer:polyvinyl chloride will be 15:30:55.

Figure 5:
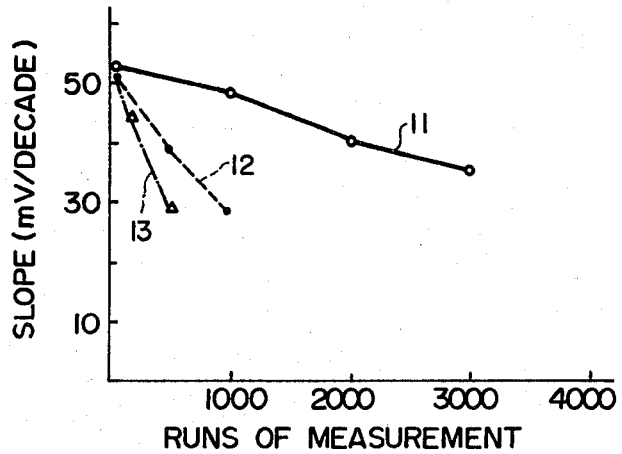
FIG. 5 is a diagram showing changes in slope in comparison when serum is measured by anion sensing electrodes having polymeric membranes of different plasticizers.

FIG. 5 is a diagram showing a change in slope when serum samples were measured by anion sensing electrodes provided with polymeric sensing membranes containing different plasticizers, where curve 11 shows the results of a sensing membrane of quaternary ammonium salt/n-tetradecyl alcohol/polyvinyl chloride system, and curve 12 and curve 13 show results of using dioctyl phthalate and dioctyl adipate, respectively, as a plasticizer, while using the same sensing substance and the same membrane support substance. These data are based on measurement of chloride ions in 3,000 runs of serum samples. Electrode 11 provided with a membrane containing n-tetradecyl alcohol as a plasticizer can withstand the measurement of 3,000 runs of serum sample, and thus has a long electrode life, whereas other electrodes 12 and 13 can be applied only to less than 1,000 runs of serum samples, and the function as the anion sensing electrode is lost in a short period of time.

Microscopic observation of electrodes used in the tests of FIG. 5 has revealed that the amount of inhibiting substances deposited on the membrane surface is considerably small in electrodes 11 with the membranes containing n-tetradecyl alcohol, as compared with other electrodes. It has been found that the electrodes with a smaller amount of deposited inhibiting substances such as protein have a small measurement error and a long electrode life.

What is claimed is:

1. An anion sensing electrode which comprises a vessel means containing an inner filling solution; an internal electrode in contact with the inner filling solution; a sensing membrane fixed to the vessel means, said sensing membrane containing a polymeric substance as a support substance, a quaternary ammonium salt as a sensing substance and normal tetradecyl alcohol as a plasticizer.

2. An anion sensing electrode according to claim 1, wherein the sensing membrane comprises 10-20% by weight of the sensing substance, 20-40% by weight of the alcohol and 40-60% by weight of the support substance, making total 100% by weight.

3. An anion sensing electrode according to claim 1 or 2, wherein the quaternary ammonium salt is an aliphatic ammonium salt having alkyl groups of 8 to 16 carbon atoms.

4. An anion sensing electrode according to claim 1 or 2, wherein the support substance is selected from polyvinyl chloride, polycarbonate, and silicone rubber.

5. An anion sensing electrode, which comprises a vessel means containing an inner filling solution; an internal electrode in contact with the inner filling solution; and a sensing membrane fixed to the vessel means, the sensing membrane comprising a polymeric substance as a support substance, a quaternary ammonium salt as a sensing substance and normal tetradecyl alcohol as a plasticizer; the content of the support substance being not more than 60% by weight and the content of the plasticizer being more than the content of the sensing substance.

6. An anion sensing electrode according to claim 5, wherein the vessel means is a cylinder comprising polyvinyl chloride.

7. An anion sensing electrode according to claim 6 or 5, wherein the sensing membrane comprises 55% by weight of the support substance, 15% by weight of the sensing substance, and 30% by weight of the plasticizer.

8. An anion sensing electrode according to claim 1 or claim 5, wherein the quaternary ammonium salt is selected from the group consisting of methyl-n-tridodecyl ammonium chloride, methyl-n-tetradecyl ammonium chloride, and methyl-n-trioctyl ammonium chloride and the support substance is polyvinyl chloride.

9. An anion sensing electrode according to claim 1 or claim 8, wherein said sensing membrane comprises an admixture of the support substance, the sensing substance and the plasticizer in the form of a sheet.

10. An anion sensing electrode according to claim 5, wherein the sensing membrane comprises 40 to 60% by weight of the support substance and the ratio of the plasticizer to the sensing substance is at least 1.5.

11. An anion sensing electrode according to claim 3, wherein the support substance is selected from polyvinyl chloride, polycarbonate, and silicone rubber.

* * * * *